United States Patent
Iida et al.

(10) Patent No.: US 7,347,979 B2
(45) Date of Patent: Mar. 25, 2008

(54) GAS PROCESSING METHOD AND GAS PROCESSING APPARATUS UTILIZING OXIDATION CATALYST AND LOW-TEMPERATURE PLASMA

(75) Inventors: Akemitsu Iida, Tokyo (JP); Akira Mizuno, Aichi (JP)

(73) Assignee: Nittetsu Mining Co., Ltd., Tokyo (JP)

( * ) Notice: Subject to any disclaimer, the term of this patent is extended or adjusted under 35 U.S.C. 154(b) by 137 days.

(21) Appl. No.: 10/560,980

(22) PCT Filed: Mar. 30, 2004

(86) PCT No.: PCT/JP2004/004521

§ 371 (c)(1),
(2), (4) Date: Dec. 16, 2005

(87) PCT Pub. No.: WO2004/112940

PCT Pub. Date: Dec. 29, 2004

(65) Prior Publication Data

US 2007/0098614 A1    May 3, 2007

(30) Foreign Application Priority Data

Jun. 17, 2003  (JP) .................... 2003-172553

(51) Int. Cl.
*A61L 9/00* (2006.01)
*A61L 9/16* (2006.01)
*B01J 19/08* (2006.01)
*H05H 1/24* (2006.01)

(52) U.S. Cl. .................... 423/210; 422/4; 422/5; 422/28; 422/168; 422/177; 422/180; 422/186.04; 422/186.18; 204/164

(58) Field of Classification Search ............... 423/210, 423/230, 244.01, 244.09, 244.1, 247, 239.1, 423/245.1, 245.3; 422/168, 177, 180, 186.07, 422/186.18, 186.04, 4, 5, 28; 204/164
See application file for complete search history.

(56) References Cited

U.S. PATENT DOCUMENTS 3,983,021 A * 9/1976 Henis .................... 204/164

(Continued)

FOREIGN PATENT DOCUMENTS

CN    2351151 Y    12/1999

(Continued)

OTHER PUBLICATIONS

Database WPI Week 200156, Derwent Publications Ltd., London, GB; AN 2001-505792, XP002427901.

(Continued)

*Primary Examiner*—Timothy C. Vanoy
(74) *Attorney, Agent, or Firm*—Sughrue Mion, PLLC

(57) ABSTRACT

A method for treating a gas characterized in that a low temperature plasma is generated in the presence of a metallic oxide oxidation catalyst, and an apparatus for treating a gas characterized by containing a low temperature plasma-generating unit carrying a metallic oxide oxidation catalyst are disclosed. According to the treating method and the treating apparatus, harmful components (such as carbon monoxide or a volatile organic compound) in a gas to be treated can be efficiently oxidized and rendered harmless, a foul odor may be rendered odorless, and further, microorganisms may be removed from and reduced in the treated gas.

10 Claims, 6 Drawing Sheets

U.S. PATENT DOCUMENTS

| | | | |
|---|---|---|---|
| 4,871,515 A | 10/1989 | Reichle et al. | |
| 5,637,198 A | 6/1997 | Breault | |
| 5,711,147 A * | 1/1998 | Vogtlin et al. | 60/274 |
| 5,843,288 A | 12/1998 | Yamamoto | |
| 5,891,220 A | 4/1999 | Gary | |
| 7,011,796 B2 * | 3/2006 | Raybone et al. | 422/186.04 |
| 7,070,744 B2 * | 7/2006 | Son | 422/186.04 |
| 2003/0051993 A1 | 3/2003 | Ricatto et al. | |
| 2003/0098230 A1 | 5/2003 | Carlow et al. | |
| 2003/0150709 A1 | 8/2003 | LaBarge et al. | |
| 2003/0170154 A1 * | 9/2003 | Inman et al. | 422/186.04 |

FOREIGN PATENT DOCUMENTS

| | | |
|---|---|---|
| DE | 196 11 332 A1 | 9/1957 |
| DE | 42 09 196 C1 | 7/1993 |
| DE | 195 34 950 A1 | 3/1997 |
| EP | 0 716 274 A1 | 6/1996 |
| EP | 0 608 619 B1 * | 10/1997 |
| EP | 0 902 721 B1 | 3/1999 |
| GB | 2 270 013 A * | 3/1994 |
| JP | 05-309231 | 11/1993 |
| JP | 5-309231 A | 11/1993 |
| JP | 06-91138 | 4/1994 |
| JP | 6-91138 A | 4/1994 |
| JP | 8-24576 A | 1/1996 |
| JP | 8-266629 A | 10/1996 |
| JP | 08-266854 | 10/1996 |
| JP | 8-266854 A | 10/1996 |
| JP | 10-137530 A | 8/1998 |
| JP | 2001-159309 | 6/2001 |
| JP | 2001-159309 A | 6/2001 |
| JP | 2001-179040 | 7/2001 |
| JP | 2001-179040 A | 7/2001 |
| JP | 2002-336653 | 11/2002 |
| JP | 2002-336653 A * | 11/2002 |
| WO | WO 98/02233 | 1/1998 |
| WO | WO 99/38603 | 8/1999 |
| WO | WO 03/078958 A2 | 9/2003 |
| WO | WO 2004/014439 A2 | 2/2004 |

OTHER PUBLICATIONS

Yamamoto T. et al, "*Catalysis-assisted plasma technology for carbon tetrachloride destruction*", Industry Applications Society Annual Meeting, 1994, Conference Record of the 1994 IEEE Denver, CO, USA Oct. 2-6, 1994, New York, NY, USA, IEEE, Oct. 2, 1994, pp. 1556-1562.

Y. Maeda, "*Outline and Performance of Plasma Deodorizer*", Takuma Giho, vol. 5, No. 1, pp. 66-71, 1997, abstract.

* cited by examiner

GAS PROCESSING METHOD AND GAS PROCESSING APPARATUS UTILIZING OXIDATION CATALYST AND LOW-TEMPERATURE PLASMA

TECHNICAL FIELD

The present invention relates to a method and an apparatus for treating a gas wherein an oxidation catalyst (for example, an oxidation catalyst containing a metallic oxide such as manganese oxide and copper oxide, in particular, a hopcalite catalyst), and a low temperature plasma are used. According to the present invention, an activity of the metallic oxide oxidation catalyst is enhanced by the low temperature plasma, and thus, harmful components (such as carbon monoxide or a volatile organic compound) in a gas to be treated can be efficiently oxidized and rendered harmless, and a foul odor may be rendered odorless. In addition, microorganisms may be removed from and reduced in the treated gas.

BACKGROUND ART

The hopcalite catalyst is an oxidation catalyst composed of manganese oxide, copper oxide, and other metallic oxides (such as potassium oxide, silver oxide, or cobalt oxide), and it is known to oxidize and remove carbon monoxide, to clarify sulfur dioxide gas, hydrogen chloride, hydrogen sulfide, or nitrogen oxides, and to remove formaldehyde.

Concrete techniques for treating a gas with the hopcalite catalyst are known. For example, a method wherein the hopcalite catalyst is used as an adsorbent for carbon monoxide to produce an air having properties for a medical application [Japanese Unexamined Patent Publication (Kokai) No. 8-266629], a method wherein the hopcalite catalyst is used as an adsorbent for carbon monoxide, an impurity in an inert gas [Japanese Unexamined Patent Publication (Kokai) No. 10-137530], or a method wherein the hopcalite catalyst is used as a catalyst for removing odor components in a fuel gas [Japanese Unexamined Patent Publication (Kokai) No. 8-24576] are known.

Further, deodorizing techniques with a low temperature plasma are known. For example, an apparatus for a deodorization with the low temperature plasma, composed of a high voltage discharge unit capable of generating a low temperature plasma and a catalyst unit in which a pro-oxidant catalyst is loaded is known (Takuma Giho, Vol.5, No.1, 66-71, 1997). Further, a method for removing an organic solvent, utilizing a low temperature plasma, and a method for removing nitrogen oxides, utilizing a low temperature plasma, as an oxidative effect of a gas are known. In particular, however, a method for converting carbon monoxide in a gas to carbon dioxide, utilizing a low temperature plasma is not known. Further, a technique using the hopcalite catalyst and the low temperature plasma at the same time is not known. Therefore, an enhancement of an activity of the hopcalite catalyst by a low temperature plasma is not known.

DISCLOSURE OF THE INVENTION

The inventors of the present invention engaged in intensive research to develop a technique for efficiently rendering a gas containing harmful components (such as, carbon monoxide, nitrogen monoxide compounds) harmless, and as a result, found that an activity of a metallic oxide oxidation catalyst (such as, a hopcalite catalyst) is enhanced by a low temperature plasma, and that the low temperature plasma is generated in the presence of the metallic oxide oxidation catalyst (such as, the hopcalite catalyst) and a gas containing harmful components is treated therewith, whereby carbon monoxide is oxidized to carbon dioxide at a high efficiency, nitrogen monoxide is oxidized to nitrogen dioxide at a high efficiency, and further volatile organic compounds (VOC) are decomposed to carbon dioxide and water at a high efficiency, due to the enhanced activity of the metallic oxide oxidation catalyst (such as, the hopcalite catalyst) and the function of the low temperature plasma, and furthermore, a foul odor is eliminated.

The present invention is based on the above findings.

Accordingly, the present invention relates to a method for treating a gas characterized in that a low temperature plasma is generated in the presence of a metallic oxide oxidation catalyst, for example, an oxidation catalyst containing a metallic oxide, such as manganese oxide and copper oxide, particularly, a hopcalite catalyst, or an activated manganese dioxide.

According to a preferable embodiment of the treatment method of the present invention, a gas is oxidized and, for example, harmful components, such as carbon monoxide or nitrogen monoxide, in a gas to be treated are oxidized, respectively, volatile organic compounds are decomposed, or a foul odor is eliminated.

The present invention also relates to an apparatus for treating a gas characterized by containing a low temperature plasma-generating unit carrying a metallic oxide oxidation catalyst, for example, an oxidation catalyst containing a metallic oxide, such as manganese oxide and copper oxide, particularly, a hopcalite catalyst, or an activated manganese dioxide.

According to a preferable embodiment of the treatment apparatus of the present invention, the low temperature plasma-generating unit contains a hollow-cylindrical electrode and a bar electrode placed at a central axis of the hollow-cylindrical electrode, and the metallic oxide oxidation catalyst is carried on an inner surface of the hollow-cylindrical electrode while a surface of the granular catalyst is exposed, or packed between the hollow-cylindrical electrode and the bar electrode.

According to another preferable embodiment of the treatment apparatus of the present invention, the low temperature plasma-generating unit contains a hollow-cylindrical insulator, a hollow-cylindrical electrode mounted on the hollow-cylindrical insulator while an outer surface of the hollow-cylindrical insulator comes into direct contact with the hollow-cylindrical insulator, plural band electrodes arranged on an inner surface of the hollow-cylindrical insulator, and a metallic oxide oxidation catalyst arranged on the inner surface of the hollow-cylindrical insulator, the band electrodes are arranged parallel to each other in an axial direction of the hollow-cylindrical insulator on the inner surface thereof, and the metallic oxide oxidation catalyst is carried between the band electrodes while the surface of the granular catalyst is exposed, or packed within the hollow-cylindrical insulator.

According to still another preferable embodiment of the treatment apparatus of the present invention, the low temperature plasma-generating unit contains many solid-cylindrical electrodes in a housing as two separately divided groups between which an electric-discharge can be carried out, and a metallic oxide oxidation catalyst is carried on a surface of the solid-cylindrical electrode while a surface of the catalyst is exposed, or packed within the housing.

According to still another preferable embodiment of the treatment apparatus of the present invention, the low temperature plasma-generating unit contains, in a housing, (a) a solid-cylindrical protecting electrode containing a core electrode and a hollow-cylindrical insulating sheath surrounding a circumference of the core electrode, and (b) a conductive mesh electrode, and a metallic oxide oxidation catalyst is carried on the conductive mesh electrode while a surface of the catalyst is exposed, or packed within the housing.

BEST MODE FOR CARRYING OUT THE INVENTION

Figure 1:
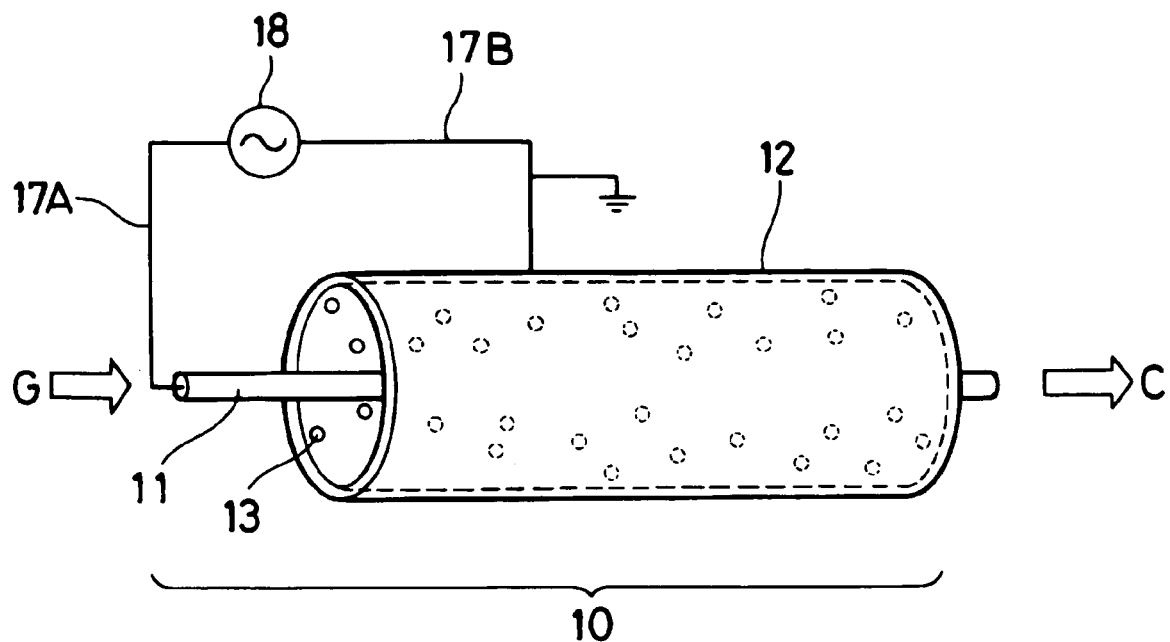
FIG. 1 is a schematic perspective view of an apparatus for generating a low temperature plasma according to the present invention, wherein metallic oxide oxidation catalysts are dispersed and carried on a cylindrical inner surface of a coaxial hollow-cylindrical low temperature plasma-generating unit containing a hollow-cylindrical electrode and a bar electrode.

A gas which is treated by the method or the apparatus according to the present invention, that is, a gas to be treated, is not particularly limited, so long as it is a gaseous compound (i.e., inorganic compound or organic compound) which may be oxidized. For example, as inorganic compounds, there may be mentioned carbon monoxide, sulfur dioxide gas, hydrogen sulfide, or nitrogen oxides (such as nitrogen monoxide), and as organic compounds, there may be mentioned volatile organic compounds (VOC). Further, the gas to be treated includes, for example, air. Gas inorganic compounds or gas organic compounds which may present as a mixture in air and may be oxidized can be treated.

The method or the apparatus according to the present invention is suitable for treating a gas (such as polluted air) containing harmful components (such as carbon monoxide, nitrogen monoxide, and/or the volatile organic compounds), particularly, a gas containing the harmful components at low concentrations. The term "low concentration" as used herein means preferably 1 ppm or less, more preferably 0.5 ppm or less for each of the above-mentioned compounds which may be oxidized, particularly, carbon monoxide, nitrogen monoxide, or the volatile organic compounds. The volatile organic compounds (VOC) include, for example, alcohols, ketones, esters, ethers, or aromatic compounds, such as phenol, toluene, styrene, or benzene.

In the present invention, the above-mentioned gas is treated with the low temperature plasma in the presence of the metallic oxide oxidation catalyst (such as the hopcalite catalyst), whereby carbon monoxide contained in the gas to be treated can be effectively converted to carbon dioxide and thus rendered harmless, and independently thereupon, nitrogen monoxide can be effectively converted to nitrogen dioxide which may be easily adsorbed and chemically treated, and further independently thereupon, the VOC can be effectively decomposed, for example, converted to carbon dioxide and water, and rendered harmless. The low temperature plasma used in the present invention can be generated by conventional methods, for example, by a discharge. As the discharge, there may be mentioned, for example, a microwave discharge, an alternating-current discharge, or a direct-current discharge.

A pair of electrodes used in the discharging methods as mentioned above includes parallel hollow-cylindrical electrodes, a coaxial hollow-cylindrical electrode/a bar electrode, spherical gap electrodes, parallel plate electrodes, a hollow-cylindrical electrode/a plain plate electrode, surface discharge electrodes, or special electrodes such as blade-type electrodes. For example, when a space between the electrodes used in the discharge therebetween is about 10 mm, an alternating voltage of over ten kV to several tens kV can be applied between the electrodes and a plasma can be generated in the gas between the electrodes.

In the present invention, for example, a conventional oxidation catalyst containing manganese oxide and copper oxide, such as a hopcalite catalyst, can be used as the metallic oxide oxidation catalyst. The metallic oxide oxidation catalyst includes the hopcalite catalyst, or the activated manganese dioxide. The hopcalite catalyst is prepared as mentioned above, by drying or sintering a granulated mixture of manganese oxide, copper oxide, and other metallic oxides (such as, potassium oxide, silver oxide, or cobalt oxide). A shape of the metallic oxide oxidation catalyst (such as, the hopcalite catalyst) used in the present invention is not particularly limited, but in general, may be powdery or granular, for example, of grains having a particle size of about 1 to 3 mm.

In the present invention, an arrangement of the metallic oxide oxidation catalysts (such as, the hopcalite catalysts) is not limited with respect to the position of the electrodes for generating the low temperature plasma, so long as an activity of the metallic oxide oxidation catalysts can be enhanced by the low temperature plasma. For example, the metallic oxide oxidation catalysts can be carried on the surfaces of the entire electrodes or a part of the electrodes for generating the low temperature plasma. When the catalysts are carried on the surfaces of a part of the electrodes, they can be carried on the surfaces of any part of both pairs of the electrodes (such as non-grounded electrodes and grounded electrodes) used for the discharge, or they can be carried on an entire surface of a part of the surfaces of one of pairs of the electrodes (such as non-grounded electrodes and grounded electrodes) used for the discharge.

An adhesive agent can be used to carry the metallic oxide oxidation catalyst (such as the hopcalite catalyst) on the surface of the electrode. For example, the powdery or granular hopcalite catalysts can be fixed by coating the adhesive agent on the entire surfaces or a part of the surfaces of the solid-cylindrical electrode, and sprinkling catalysts. In this case, at least a part of the surfaces of the powdery or granular hopcalite catalysts is preferably exposed so that the gas to be treated can come into contact therewith, more preferably the surfaces are exposed to the largest possible extent.

The electrode can have a shape, for example, a mesh shape, suitable for carrying the powdery or granular metallic oxide oxidation catalyst (such as the hopcalite catalyst) and having permeability. For example, the granular hopcalite catalysts can be put on mesh flat plate electrodes which are parallel placed and have a sieve less than the particle size of the granular hopcalite catalysts so that the gas to be treated can come into contact with substantially the entire surfaces of the granular hopcalite catalysts. If necessary, an adhesive agent can be used to fix the catalysts to the mesh flat plate electrodes so that the electrodes can be arranged in a direction other than the horizontal direction, for example, in a vertical direction. Further, an electrode having a 3D-structural body (for example, a cylindrical body) of a mesh and containing the granular hopcalite catalysts encapsulated therein may be used.

Preferably, the granular hopcalite catalysts are mounted on a surface of a grounded electrode, when a pair of the electrodes for a discharge is a combination of a non-grounded electrode and a grounded electrode, and the granular catalysts are carried or put on the surfaces of the electrodes.

The powdery or granular metallic oxide oxidation catalyst (such as, the hopcalite catalyst) can be carried on a portion other than the surface of the electrode, for example, a surface of an insulating part in the surface discharge electrode. In this case, the powdery or granular metallic oxide oxidation catalysts can be carried on the portion other than the electrode surfaces, and further carried or mounted on the electrode surfaces.

Further, in the present invention, the metallic oxide oxidation catalysts (particularly, the powdery or granular metallic oxide oxidation catalysts) can be packed in the low temperature plasma-generating unit. In this case, the metallic oxide oxidation catalysts must be packed so that the gas to be treated can pass therethrough. Further, a means, such as a filter or a cap, for preventing the powdery or granular metallic oxide oxidation catalysts from dropping out of the low temperature plasma-generating unit, is preferably placed thereat.

Concrete embodiments of the arrangement of the hopcalite catalysts as the metallic oxide oxidation catalysts in the electrodes for generating the low temperature plasma will be explained hereinafter, referring to the attached drawings.

Figure 2:
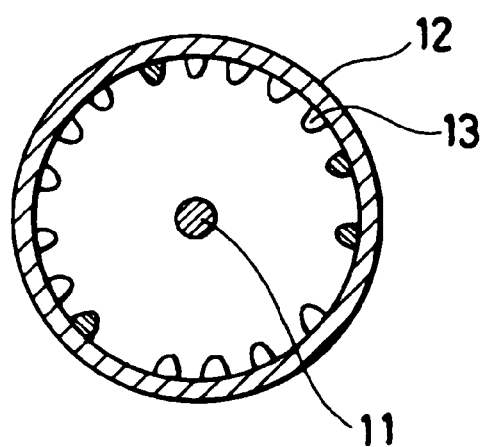
FIG. 2 is a schematic sectional view of the apparatus for generating a low temperature plasma of FIG. 1.

FIG. 1 is a schematic perspective view of an apparatus 10 for generating a low temperature plasma according to the present invention, wherein the metallic oxide oxidation catalysts are dispersed and carried on the cylindrical inner surface of the coaxial hollow-cylindrical low temperature plasma-generating unit containing the hollow-cylindrical electrode and the bar electrode. FIG. 2 is a schematic sectional view thereof. The apparatus 10 for generating the low temperature plasma contains the hollow-cylindrical electrode 12, and the bar electrode 11 located at a central axial position of the hollow-cylindrical electrode 12. On the inner surface of the hollow-cylindrical electrode 12, many granular hopcalite catalysts 13 are carried in an appropriate manner (for example, with an adhesive agent or the like) such that the surfaces of the granular catalysts are exposed. The gas G to be treated is incorporated from one opening of the hollow-cylindrical electrode 12, and the treated gas C is discharged from the other opening.

In this embodiment, it is not necessary to ground either of the bar electrode 11 or the hollow-cylindrical electrode 12. However, in view of safety while working, it is preferable to ground one of the electrodes. In the case that one of the electrodes is grounded, preferably the bar electrode 11 is not grounded, whereas the hollow-cylindrical electrode 12 is grounded. In this case, the non-grounded bar electrode 11 is connected to an electric wire 17A, the grounded hollow-cylindrical electrode 12 is connected to the grounded electric wire 17B, and both of the electric wires 17A, 17B are connected to an alternating-current power supply 18 (shown in FIG. 1 only) which applies a high voltage between the non-grounded bar electrode 11 and the grounded hollow-cylindrical electrode 12.

Figure 3:
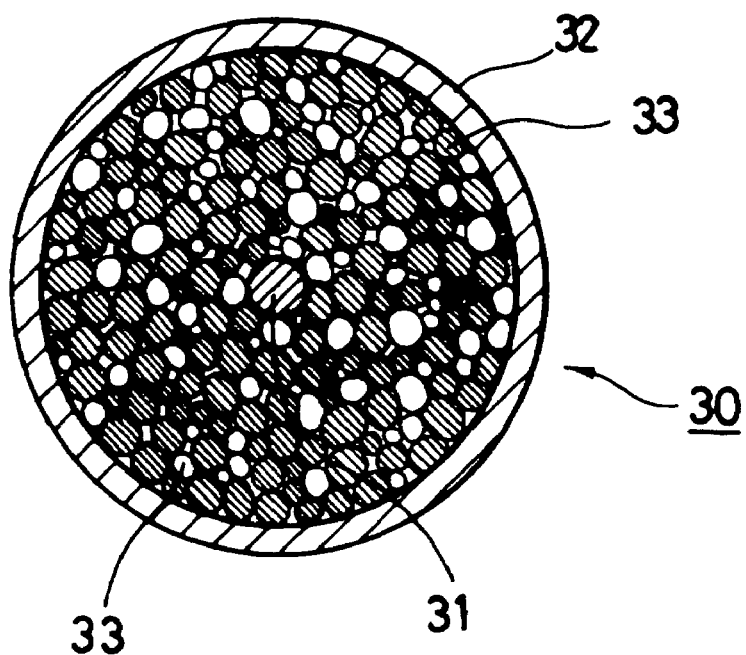
FIG. 3 is a schematic sectional view of the apparatus for generating a low temperature plasma according to the present invention, wherein metallic oxide oxidation catalysts are packed in a cylindrical inside of a coaxial hollow-cylindrical low temperature plasma-generating unit, as shown in FIG. 1, which contains a hollow-cylindrical electrode and a bar electrode.

FIG. 3 is a schematic sectional view of the apparatus 30 for generating a low temperature plasma according to the present invention, wherein metallic oxide oxidation catalysts are packed in a cylindrical inside of a coaxial hollow-cylindrical low temperature plasma-generating unit, as shown in FIG. 1, which contains a hollow-cylindrical electrode and a bar electrode. As the apparatus 10 for generating the low temperature plasma, the apparatus 30 for generating the low temperature plasma contains the hollow-cylindrical electrode 32, and the bar electrode 31 located at the central axial position of the hollow-cylindrical electrode 12. In contrast to the apparatus 10 for generating the low temperature plasma, many granular hopcalite catalysts 33 are packed in the inner space of the hollow-cylindrical electrode 32. Preferably, filters or the like are placed at the opening (not shown) for incorporating the gas to be treated and the opening (not shown) for discharging the treated gas for preventing the granular hopcalite catalysts 33 from dropping out. The gas G (not shown) to be treated is incorporated from one opening of the hollow-cylindrical electrode 32 and the treated gas C (not shown) is discharged from the other opening thereof.

In this embodiment, it is not necessary to ground either the bar electrode 31 or the hollow-cylindrical electrode 32. However, in view of safety while working, it is preferable to ground one of the electrodes. In the case that one of the electrodes is grounded, preferably the bar electrode 31 is not grounded, whereas the hollow-cylindrical electrode 32 is grounded. In this case, the non-grounded bar electrode 31 is connected to an electric wire (not shown), the grounded hollow-cylindrical electrode 32 is connected to the grounded electric wire (not shown), and both of the electric wires are connected to an alternating-current power supply (not shown) which applies a high voltage between the non-grounded bar electrode 31 and the grounded hollow-cylindrical electrode 32.

Figure 4:
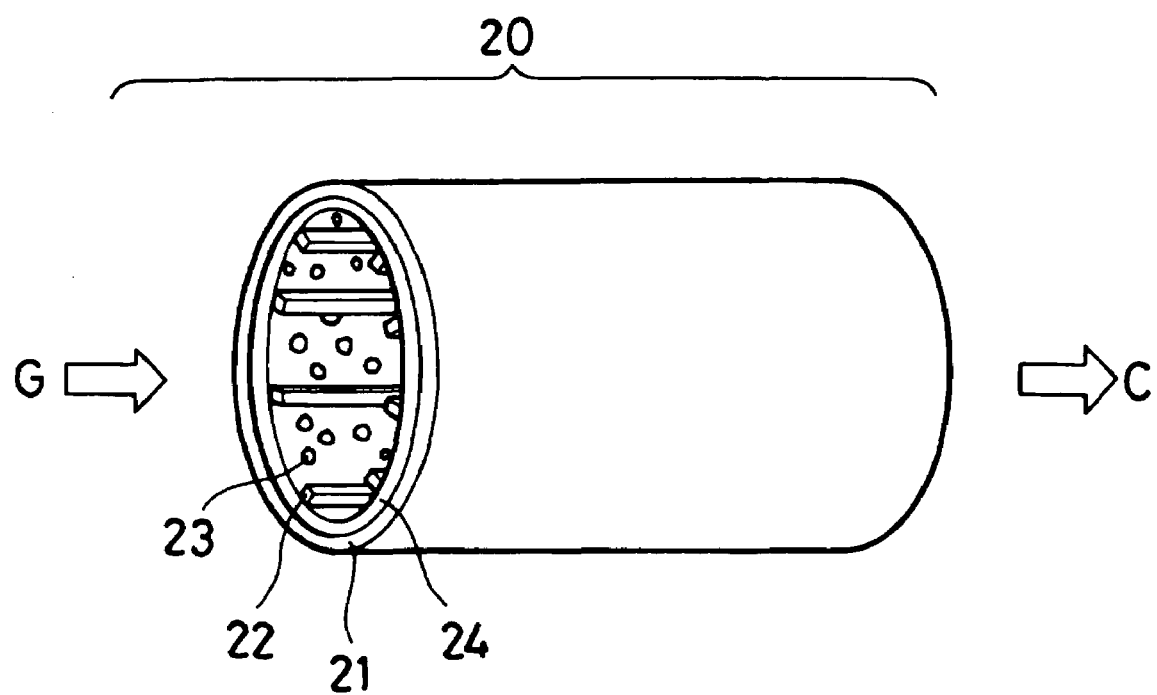
FIG. 4 is a schematic perspective view of an apparatus for generating a low temperature plasma according to the present invention, wherein metallic oxide oxidation catalysts are dispersed and carried on a cylindrical inner surface of a surface discharging type low temperature plasma-generating unit containing a hollow-cylindrical electrode and band electrodes.
Figure 5:
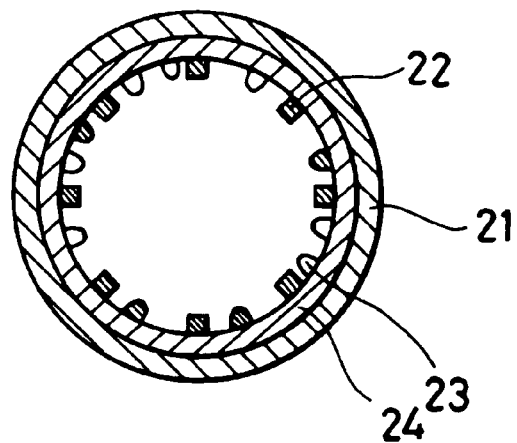
FIG. 5 is a schematic sectional view of the surface discharging type low temperature plasma-generating apparatus of FIG. 4.

FIG. 4 is a schematic perspective view of an apparatus 20 for generating a low temperature plasma by a surface discharge, and FIG. 5 is a schematic sectional view thereof.

The apparatus 20 for generating the low temperature plasma contains the hollow-cylindrical insulator 24 and the hollow-cylindrical electrode 21. The hollow-cylindrical electrode 21 comes into direct contact with the outer surface of the hollow-cylindrical insulator 24. Further, plural band electrodes 22 and many granular hopcalite catalysts 23 are located on the inner surface of the hollow-cylindrical insulator 24. The band electrodes 22 are arranged parallel to each other in an axial direction on the inner surface of the hollow-cylindrical insulator 24. Many granular hopcalite catalysts 23 are carried between the band electrodes 22 in an appropriate manner, such as by an adhesive agent. The gas G to be treated is incorporated from one opening of the hollow-cylindrical insulator 24 and the treated gas C is discharged from the other opening.

In this embodiment, it is not necessary to ground either of the hollow-cylindrical electrode 21 or the bar electrodes 22. However, in view of safety while working, it is preferable to ground one of the electrodes. In the case that one of the electrodes is grounded, preferably the hollow-cylindrical electrode 21 is not grounded, whereas the bar electrodes 22 are grounded. In this case, although a power supply and electric wires are not shown in FIGS. 4 and 5, the non-grounded hollow-cylindrical electrode 21 is connected to an electric wire, the grounded bar electrodes 22 are connected to the grounded electric wire, and both of the electric wires are connected to an alternating-current power supply which applies a high voltage between the hollow-cylindrical electrode and the grounded bar electrodes 22.

As in the apparatus 30 for generating the low temperature plasma as shown in FIG. 3, many granular hopcalite catalysts can be packed in an inside of a hollow-cylindrical insulator of an apparatus for generating the low temperature plasma containing a hollow-cylindrical insulator, a hollow-cylindrical electrode, and band electrodes, as the apparatus 20 for generating the low temperature plasma as shown in FIGS. 4 and 5. In this case, preferably, filters or the like are placed at the opening for incorporating the gas to be treated and the opening for discharging the treated gas.

Figure 6:
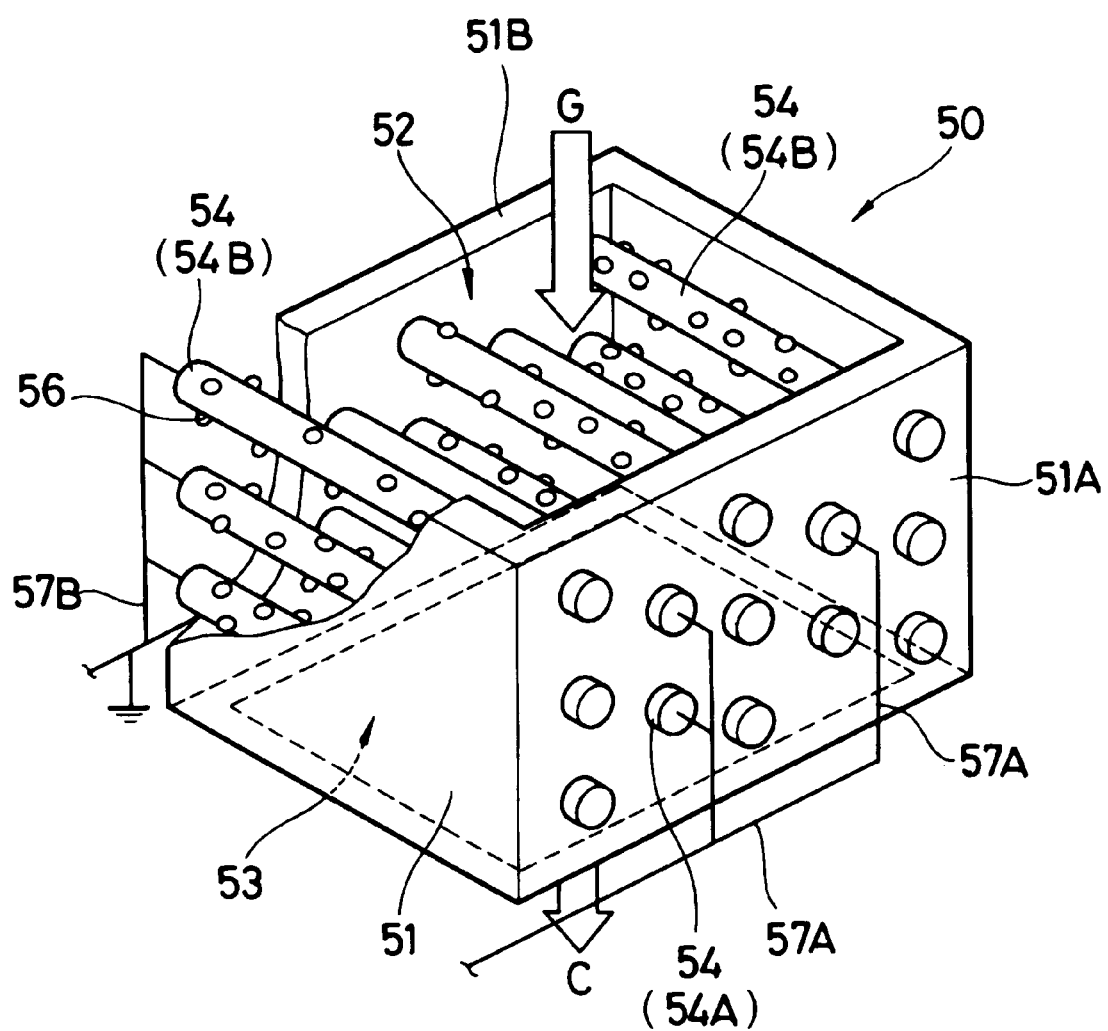
FIG. 6 is a schematic perspective view of an apparatus for generating a low temperature plasma according to the present invention, wherein metallic oxide oxidation catalysts are dispersed and carried on surfaces of groups of solid-cylindrical electrodes in a low temperature plasma-generating unit having the groups of the solid-cylindrical electrodes in a housing.

FIG. 6 is a partially broken-away schematic perspective view of an apparatus 50 for generating a low temperature plasma, but with a part of sidewalls of the housing 51 broken away. The apparatus 50 for generating a low temperature plasma has a generally rectangular parallelepiped housing 51 containing an opening 52 for incorporating the gas G to be treated and an opening 53 for discharging the treated gas C. In the inside of the housing 51, many solid-cylindrical electrodes 54 are placed. The solid-cylindrical electrodes 54 are divided into two electrodes groups. It is not necessary to ground either of the two electrodes groups. However, in view of safety while working, it is preferable to ground one of the two electrodes groups. In the case that the solid-cylindrical electrodes 54 are divided into the group of non-grounded electrodes 54A and the group of grounded electrodes 54B, each of the groups is connected to the electric wires 57A, 57B, respectively, and the electric wires 57A, 57B are connected to the alternating-current power supply (not shown). The electric wire 57B connecting to the group of the grounded electrodes 54B is grounded. On the surface of the solid-cylindrical electrodes belonging to the group of the grounded electrodes 54B, many granular hopcalite catalysts 56 are carried in an appropriate manner, for example, by an adhesive agent, so that the surfaces of the catalysts are exposed. A high voltage is applied between the group of the non-grounded electrodes 54A and the group of the grounded electrodes 54B.

In the embodiment as shown in FIG. 6, the solid-cylindrical electrodes 54 may be a combination of (a) protecting electrodes (for example, solid-cylindrical glass electrodes) containing a core electrode and a hollow-cylindrical insulating sheath surrounding a circumference of the core electrode, and (b) solid-cylindrical exposed electrodes (for example, solid-cylindrical stainless steel electrodes), a surface of which is capable of coming into direct contact with a gas to be treated, or may be composed only of the protecting electrodes (a). In the case of the combination of the protecting electrodes (a) and the exposed electrodes (b), preferably, the protecting electrodes (a) are the group of non-grounded electrodes 54A, whereas the exposed electrodes (b) are the group of grounded electrodes 54B, and the granular hopcalite catalysts 56 are carried on the exposed electrodes (b).

As in the apparatus 30 for generating the low temperature plasma as shown in FIG. 3, many granular hopcalite catalysts can be packed in an inside of a housing of an apparatus for generating the low temperature plasma containing a group of solid-cylindrical electrodes in the housing, as in the apparatus 50 for generating the low temperature plasma as shown in FIG. 6. In this case, preferably, filters or the like are placed at the opening for incorporating the gas to be treated and the opening for discharging the treated gas.

Figure 7:
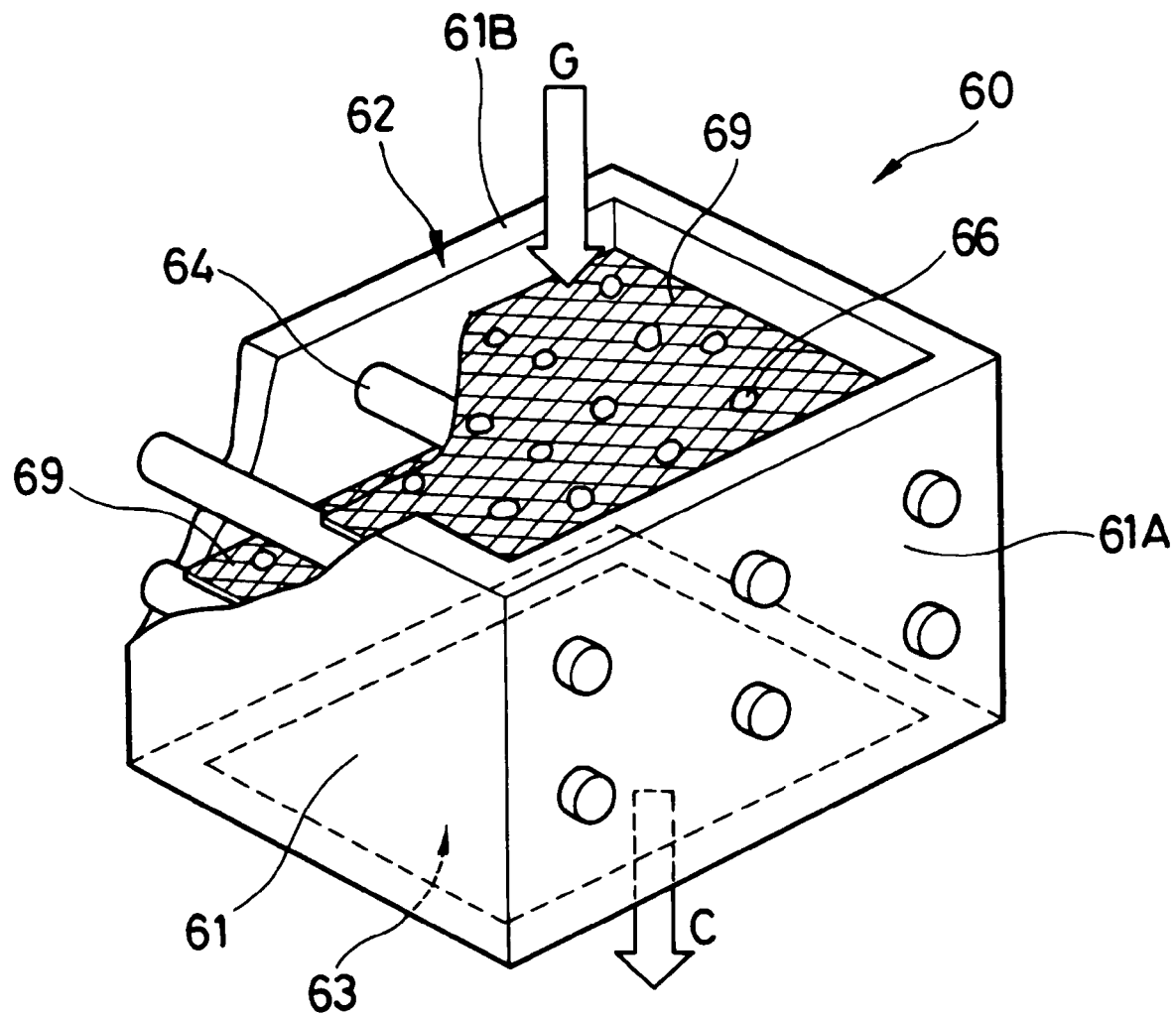
FIG. 7 is a schematic perspective view of an apparatus for generating a low temperature plasma according to the present invention, wherein metallic oxide oxidation catalysts are dispersed and carried on surfaces of groups of mesh electrodes in a low temperature plasma-generating unit having the groups of solid-cylindrical electrodes and the groups of mesh electrodes in a housing.
Figure 8:
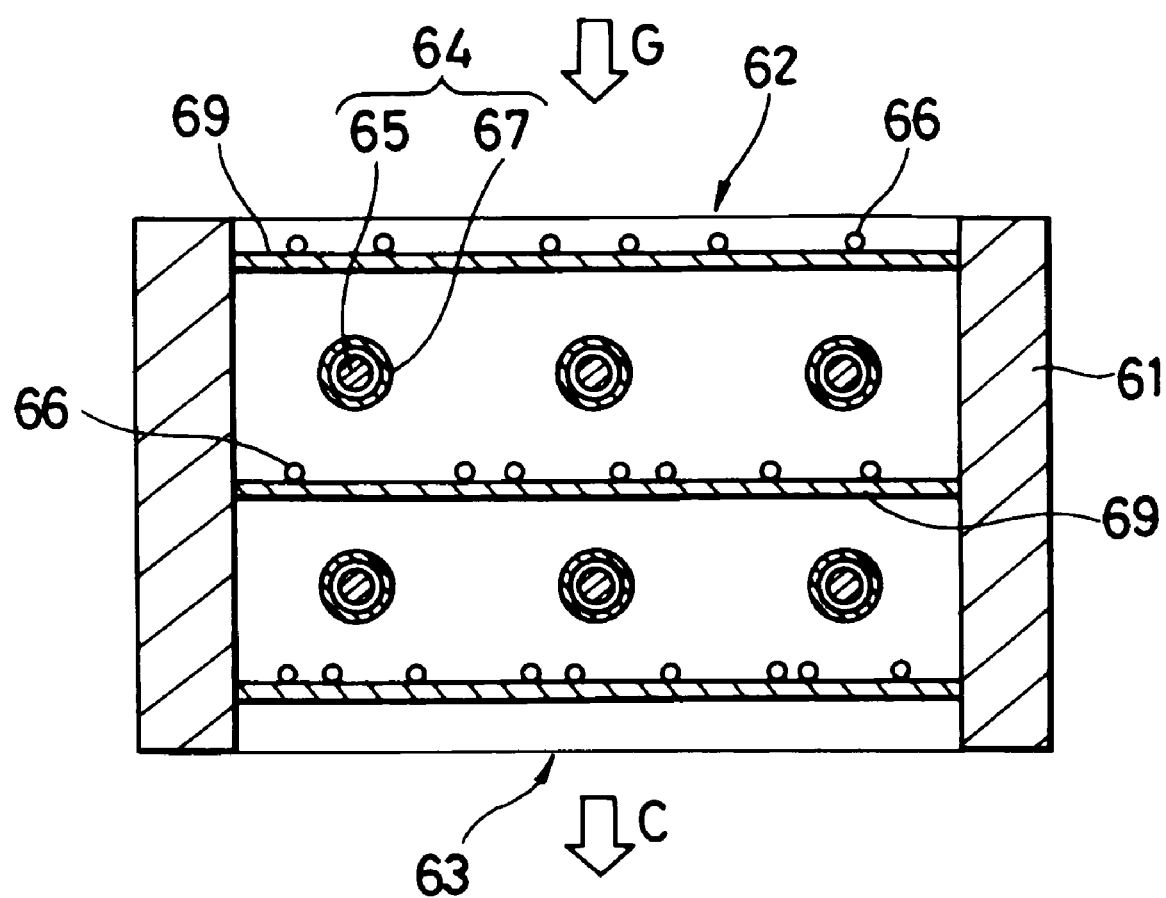
FIG. 8 is a schematic sectional view of the apparatus for generating a low temperature plasma of FIG. 7.

FIG. 7 is a partially broken-away schematic perspective view of an apparatus 60 for generating a low temperature plasma, but with a part of sidewalls of the housing 61 broken away. FIG. 8 is a schematic sectional view thereof. The apparatus 60 for generating a low temperature plasma has a generally rectangular parallelepiped housing 61 containing an opening 62 for incorporating the gas G to be treated and an opening 63 for discharging the treated gas C. In the inside of the housing 61, many solid-cylindrical electrodes 64 and plural mesh electrodes 69 are placed. Each electrode of the group of the solid-cylindrical electrodes 64 is a protecting electrode (for example, a solid-cylindrical glass electrode) containing a core electrode and a hollow-cylindrical insulating sheath surrounding a circumference of the core electrode. Each electrode of the group of the mesh electrodes 69 may be a net-type flat plate structure of an electrically conductive material, for example, a metal, such as stainless steel, titanium alloy, or nickel alloy.

Further, the mesh electrodes 69 carry many hopcalite catalysts 66 fixed thereon in an appropriate manner, for example, by an adhesive agent, so that the surfaces are exposed, or merely put on upper surfaces.

In this embodiment, it is not necessary to ground either of the group of the solid-cylindrical electrodes 64 or the group of the mesh electrodes 69. However, in view of safety while working, it is preferable to ground one group of the electrodes. In case that one group of the electrodes is grounded, preferably the group of solid-cylindrical electrodes 64 is not grounded, whereas the group of the mesh electrodes 69 is grounded. In this case, although not shown in FIGS. 7 and 8, the group of the solid-cylindrical electrodes 64 and the group of the mesh electrodes 69 are connected to electric wires, respectively, and the electric wires are connected to an alternating-current power supply. The electric wire connecting to the grounded electrodes (particularly, the group of the grounded mesh electrodes) is grounded. A high voltage is applied between the group of the solid-cylindrical electrodes 64 and the group of the mesh electrodes 69.

When the hopcalite catalysts 66 are put on the surfaces of the mesh flat plate electrodes 69 without fixing, the mesh flat plate electrodes 69 are arranged in a vertical direction as shown in FIGS. 7 and 8 so that the hopcalite catalysts 66 do not drop off. In this case, further, the mesh flat plate electrodes 69 must have a sieve less than the particle size of the granular hopcalite catalysts 66.

On the contrary, when the hopcalite catalysts 66 are carried and fixed on the surfaces of the mesh flat plate electrodes 69 in an appropriate manner, for example, by an adhesive agent, an arranging direction or the size of the sieve of the mesh flat plate electrodes 69 are not limited.

As in the apparatus 30 for generating the low temperature plasma as shown in FIG. 3, many granular hopcalite catalysts can be packed in an inside of a housing of an apparatus for generating the low temperature plasma containing solid-cylindrical electrodes and mesh electrodes, as in the apparatus 60 for generating the low temperature plasma as shown in FIGS. 7 and 8. In this case, preferably, filters or the like are placed at the opening for incorporating the gas to be treated and the opening for discharging the treated gas.

Figure 9:
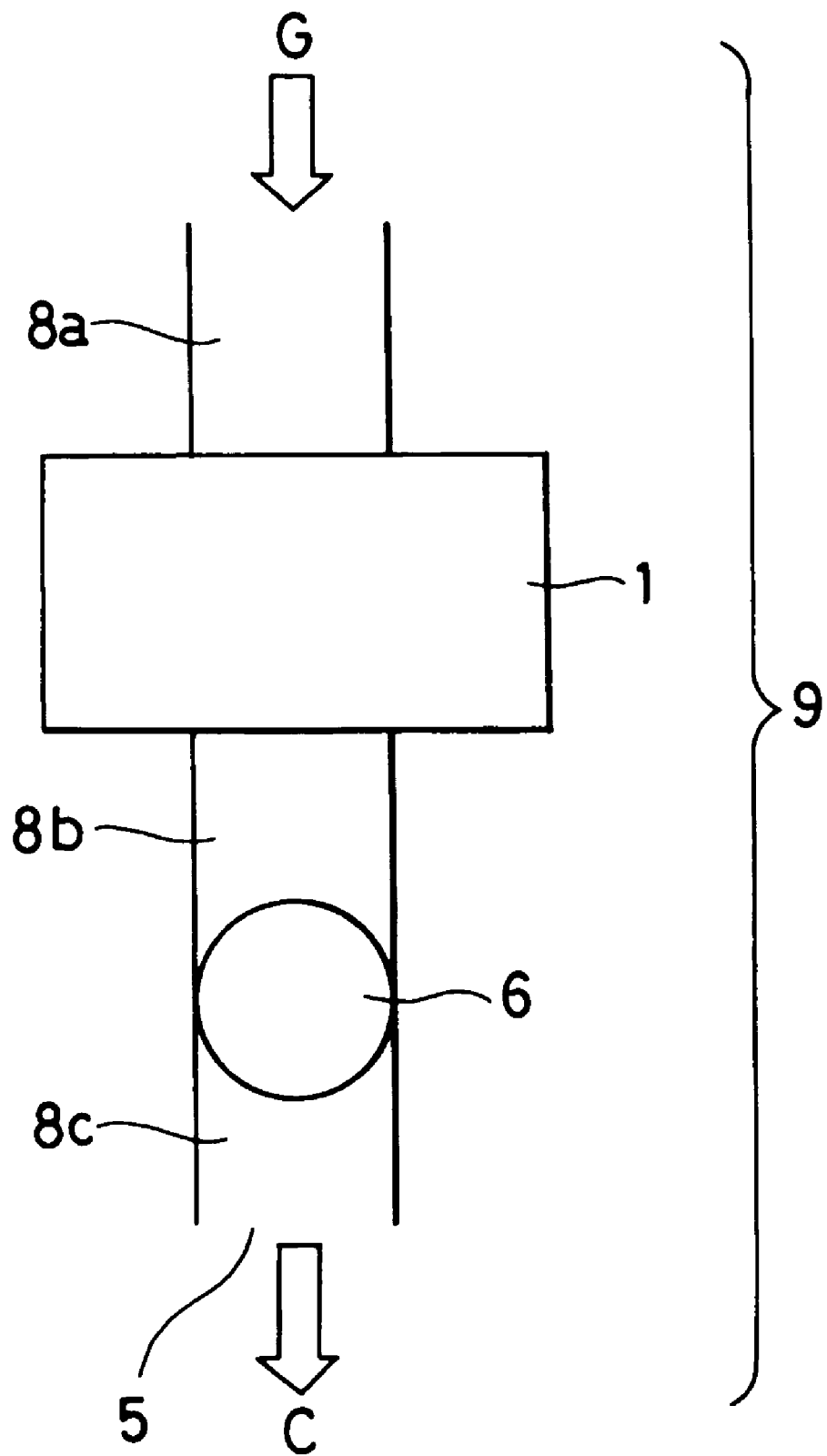
FIG. 9 is a schematic sectional view of a typical embodiment of the apparatus according to the present invention.

A typical embodiment of the apparatus of the present invention is shown in FIG. 9.

The apparatus 9 for treating a gas as shown in FIG. 9 contains the apparatus 1 for generating the low temperature plasma wherein the hopcalite catalysts are carried. The apparatus 1 for generating the low temperature plasma contains a transporting tube 8a as a supplying means capable of supplying the gas G (for example, a polluted air) whereby the gas G to be treated is incorporated into the inside of the apparatus 1 for generating the low temperature plasma. At the tip of the transporting tube 8a, an intake means (not shown) capable of continuously or intermittently taking in the gas G to be treated is installed.

Further, a transporting tube 8b is installed for conveying the treated gas C from the apparatus 1 for generating the low temperature plasma to the discharging opening 5. Furthermore, if necessary, a forced-blowing fan 6 may be installed via the transporting tube 8b, downstream of the apparatus 1 for generating the low temperature plasma. The term "downstream" or the term "upstream" as used herein means with respect to the flow direction of the gas G to be treated and the treated gas C. The discharging opening 5 for the treated gas C is installed via the transporting tube 8c, downstream of the forced-blowing fan 6. In addition to or instead of the forced-blowing fan 6, a forced-blowing fan can be installed in the transporting tube 8a.

When the gas G is treated by the gas-treating apparatus 9 as shown in FIG. 9, the gas G to be treated is incorporated from the transporting tube 8a into the inside of the apparatus 1 for generating the low temperature plasma. Then, the low temperature plasma is generated in the inside of the apparatus 1 to produce radicals by the generated low temperature plasma. Further, the activity of the hopcalite catalysts is enhanced by the low temperature plasma. Due to the functions of the radicals and the hopcalite catalysts, carbon monoxide in the gas G to be treated is efficiently oxidized to carbon dioxide, and the volatile organic compounds (VOC) are efficiently decomposed to carbon dioxide and water. A foul odor is efficiently rendered odorless at the same time.

The resulting treated gas C is discharged by the forced-blowing fan 6 through the transporting tubes 8b and 8c from the discharging opening 5. According to the gas-treating apparatus 9, the gas to be treated can be treated batchwise, or preferably, continuously. Particularly, in the continuous treatment, amounts of pollutant substances (particularly, carbon monoxide, nitrogen monoxide, and VOC) in the gas to be treated vary. Therefore, various sensors may be installed in the transporting tube 8a, the transporting tube 8b, and/or the discharging opening 5 to control the stream quantity of the gas to be treated and/or the voltage applied.

Function

The mechanism whereby the activity of the metallic oxide oxidation catalyst, such as the hopcalite catalyst, is enhanced by the low temperature plasma in the present invention has not been elucidated as yet. However, a part of the mechanism whereby carbon monoxide and nitrogen monoxide, as well as the volatile organic compounds in the gas to be treated, can be unexpectedly efficiently rendered harmless by the combined use of the metallic oxide oxidation catalyst and the low temperature plasma can be presumed as follows. In this connection, it would be noted that the present invention is not limited to the presumption as mentioned below.

When the low temperature plasma is generated, the plasma per se causes an oxidation reaction and also produces ozone. The produced ozone is reduced to an oxygen molecule in the presence of the metallic oxide oxidation catalyst whereby the reduction reaction and the oxidation reaction are caused. Therefore, it is believed that the oxidation reaction acts on carbon monoxide, nitrogen monoxide, and the volatile organic compounds in the gas to be treated. However, it is also considered that a large part of the function by the low temperature plasma stems from the generation of the radicals, and the contribution of the above oxidation is only a part of the effects obtained by the present invention.

Particularly, it is known that the hopcalite catalyst exhibits a sufficient activity when dry, but becomes inactive when wet. In the present invention, however, the hopcalite catalyst is used together with the low temperature plasma. When the low temperature plasma is generated, a temperature at the discharging electrodes is elevated. Therefore, if the humidity of the gas to be treated is relatively high, a dry state of the hopcalite catalyst can be maintained, and the deactivation of the hopcalite catalyst can be inhibited.

In the gas treating apparatus by the low temperature plasma, ozone is also generated together with radicals by the low temperature plasma. In general, most of the ozone is consumed in the gas-treating step, but a part of the ozone is sometimes not consumed but discharged together with the treated gas. The discharge of ozone is not desirable, and thus, in the conventional gas-treating apparatus using the low temperature plasma, it is necessary to install a porous adsorbent such as activated carbon for adsorbing ozone at the discharging opening. The porous adsorbent adsorbs dusts contained in the gas. Thus, the dust adsorbed in the porous adsorbent is an appropriate growth medium for microorganisms. When the gas-treating apparatus using the low temperature plasma is operated, ozone is generated and the growth of the microorganisms is inhibited. However, when the operation of the gas-treating apparatus using the low temperature plasma is stopped, the growth of the microorganisms is not inhibited, and the microorganisms grow proliferously in the porous adsorbent. When the operation of the gas-treating apparatus using the low temperature plasma is started again in this state, the microorganisms are discharged together with the treated gas. The conventional gas-treating apparatus using the low temperature plasma has such a disadvantage.

On the contrary, the metallic oxide oxidation catalyst, such as the hopcalite catalyst, used in the present invention has a function to decompose ozone. Thus, it is not necessary to install a porous adsorbent such as an activated carbon for adsorbing ozone at the discharging opening, or it is possible to reduce the amount of a porous adsorbent used. Further, in the present invention, dusts contained in the gas to be treated are adsorbed mainly on the electrode surfaces. The metallic oxide oxidation catalyst carried on the electrode surfaces has an antibacterial activity and the function of the dusts as a growth medium of the microorganisms is inhibited. Therefore, when the stopping and restarting of the operation of the apparatus of the present invention is repeated, the microorganisms are eliminated or reduced in the treated gas.

The present invention has excellent treatment effects as above, and is suitable for the treatment of a polluted air containing low concentrations of carbon monoxide, nitrogen monoxide, and/or VOC, a polluted air containing a waste gas from vehicles, an unventilated indoor air of a room wherein a combustion heater is used for a long time, or a polluted air containing cigarette smoke such as an air of a smoking room. Further, according to the present invention, microorganisms are eliminated or reduced from the treated gas, the present invention may be preferably applied to an air purification system used in an atmosphere (for example, in a medical institution or a house) requiring a supplement of a disinfectant or sterilized gas.

EXAMPLES

The present invention now will be further illustrated by, but is by no means limited to, the following Examples.

Example 1

In this Example, a gas-treatment apparatus 9 having a structure similar to that of the embodiment shown in FIG. 9 was used. As the low temperature plasma generating apparatus 1 in the gas-treatment apparatus 9, the low temperature plasma generating apparatus 50 having a structure similar to that shown in FIG. 6 was used. The apparatus 50 for generating the low temperature plasma had 74 electrodes composed of the group of grounded solid-cylindrical exposed SUS electrodes 54B carrying hopcalite catalysts (JL Science; average particle size=2 mm; apparent density=0.82 g/cm$^3$) fixed on the surfaces thereof with an adhesive agent, and the group of non-grounded solid-cylindrical glass electrodes 54A. The distance of each electrode was 4.75 mm. The hopcalite catalyst grains were carried on the surfaces of the solid-cylindrical exposed SUS electrodes 54B at a density of about 0.17 g/cm$^2$. The non-grounded solid-cylindrical glass electrode used was a protecting electrode composed of a bar aluminum core electrode (external diameter=1.5 mm) and a hollow-cylindrical glass sheath (external diameter=4 mm) and an air was filled in the glass sheath. The solid-cylindrical exposed SUS electrode used was an exposed electrode having an external diameter of 4 mm. Further, as the housing 51 in the apparatus 50 for generating the low temperature plasma, a rectangular parallelepiped (height=48 cm; width=48 cm; breadth=11 cm) of polyphenylene sulfide (PPS) was used.

As the gas to be treated, smoke emitted from smokers was gathered in a polytetrafluoroethylene (Teflon) bag and used. The gas to be treated was incorporated into the low temperature plasma generating apparatus 1 (50) in the gas-treatment apparatus 9 from the transporting tube 8a as the means for supplying the gas to be treated. The low temperature plasma was generated at an applied voltage of 8 kV at a temperature of 22° C. and humidity of 60%. Thereafter, the treated gas was discharged by the forced-blowing fan 6 via the transporting tube 8c from the discharge opening 5.

The treatment capacity was calculated as follows. A concentration of the volatile organic compounds (VOC) contained in the gas to be treated, and a concentration of the volatile organic compounds (VOC) contained in the gas treated by the gas-treatment apparatus according to the present invention were measured. From the results, the removal rates of VOC were calculated. The gas samples to be treated were taken at the opening for incorporating the gas to be treated, and the treated gas samples were taken at the opening for discharging the treated gas. The concentration of the VOC was measured by a gas chromatograph mass spectrometer (Hewlett-Packard; HP6890) equipped with a gas-concentrating apparatus (Entec; Model 7000). The results of the VOC measurements and the VOC removal rates calculated therefrom are shown in Table 1.

Comparative Example 1

The treatment capacity when the low temperature plasma was generated in the absence of the hopcalite catalyst was examined. Specifically, the procedures of Example 1 were repeated except that the gas-treating apparatus 9 equipped with a low temperature plasma generating apparatus containing the group of grounded solid-cylindrical exposed SUS electrodes without the hopcalite catalyst was used instead of the group of the grounded solid-cylindrical exposed SUS electrodes 54B carrying the hopcalite catalysts in the low temperature plasma generating apparatus 50 used in Example 1.

Concentrations of the VOC of the gas to be treated and the treated gas, and the VOC removal rates are shown in Table 1.

Comparative Example 2

The treatment capacity only by the hopcalite catalyst without generating the low temperature plasma was examined. Specifically, the procedures of Example 1 were repeated except that the gas was treated while no voltage was applied in the low temperature plasma generating apparatus 50 used in Example 1.

Concentrations of the VOC of the gas to be treated and the treated gas, and the VOC removal rates are shown in Table 1.

TABLE 1

| Condition Gas-sampling site | Example 1 Combination of hopcalite catalyst and plasma | | Comparative Example 1 Plasma only | | Comparative Example 2 Hopcalite catalyst | |
|---|---|---|---|---|---|---|
| | Inlet port (ppb) | Outlet port (ppb) | Inlet port (ppb) | Outlet port (ppb) | Inlet port (ppb) | Outlet port (ppb) |
| Benzene | 15.6 | 11 | 15.7 | 14.4 | 15.2 | 12.8 |
| Toluene | 26.3 | 16.9 | 24.8 | 22.4 | 25.3 | 21.6 |
| Ethylbenzene | 4.5 | 2.5 | 4.7 | 4.2 | 4.7 | 3.8 |
| m-, and p-Xylene | 12.4 | 6.5 | 12.7 | 10.2 | 12.9 | 10.2 |
| Styrene | 7.1 | 1.6 | 7.2 | 5.9 | 7.7 | 5.8 |
| o-Xylene | 2.7 | 1.3 | 2.8 | 2.4 | 2.8 | 2.2 |
| Total concentration of VOC | 68.6 | 39.8 | 67.9 | 59.5 | 68.6 | 56.4 |
| Removal rate | 42% | | 12% | | 18% | |

INDUSTRIAL APPLICABILITY

According to the present invention, the activity of the metallic oxide oxidation catalyst, such as the hopcalite catalyst, is enhanced by the low temperature plasma. Therefore, harmful components, such as carbon monoxide, nitrogen monoxide, or the volatile organic compounds in the gas to be treated can be effectively oxidized to be rendered harmless, and a foul odor may be rendered odorless. Further, microorganisms may be removed from and reduced in the treated gas.

Although the present invention has been described with reference to specific embodiments, various changes and modifications obvious to those skilled in the art are possible without departing from the scope of the appended claims.

The invention claimed is:

1. A method for treating polluted air containing cigarette smoke comprising the steps of introducing polluted air into a low temperature plasma-generating unit containing a hopcalite catalyst, and at least a pair of electrodes; generating a low temperature plasma in the unit to treat the polluted air, and discharging treated air.

2. The method according to claim 1, wherein a gaseous compound in the polluted air is oxidized.

3. The method according to claim 1, wherein a volatile organic compound in the polluted air is decomposed.

4. The method according to claim 1, wherein a foul odor in the polluted air is rendered to odorless.

5. An apparatus for treating a polluted air containing cigarette smoke, comprising
   a low temperature plasma-generating unit containing a hopcalite catalyst, and at least a pair of electrodes;
   a means for supplying the polluted air to the low temperature plasma-generating unit,
   a means for discharging a treated gas, and
   an alternating-current power supply for applying a high voltage between the electrodes.

6. The apparatus according to claim 5, wherein said low temperature plasma-generating unit contains a hollow-cylindrical electrode and a bar electrode placed at a central axis of said hollow-cylindrical electrode, and said hopcalite catalyst is carried on an inner surface of said hollow-cylindrical electrode in the form of granule while a surface of said granular catalyst is exposed.

7. The apparatus according to claim 5, wherein said low temperature plasma-generating unit contains a hollow-cylindrical insulator, a hollow-cylindrical electrode mounted on said hollow-cylindrical insulator while an outer surface of said hollow-cylindrical insulator comes into direct contact with said hollow-cylindrical electrode, plural band electrodes arranged on an inner surface of said hollow-cylindrical insulator, and said hopcalite catalyst arranged in the form of granule on said inner surface of said hollow-cylindrical insulator, said band electrodes being arranged parallel to each other in a direction of an axial of said hollow-cylindrical insulator on said inner surface thereof, and said hopcalite catalyst is carried between said band electrodes while the surface of the granular catalyst is exposed.

8. The apparatus according to claim 5, wherein said low temperature plasma-generating unit contains solid-cylindrical electrodes in a housing as two separately divided groups between which an electric-discharge can be carried out, and the hopcalite catalyst is carried on a surface of said solid-cylindrical electrode while a surface of said catalyst is exposed.

9. The apparatus according to claim 8, wherein said solid-cylindrical electrode
   (1) is a combination of (a) a protecting electrode containing a core electrode and a hollow-cylindrical insulating sheath surrounding a circumference of said core electrode, and (b) a solid-cylindrical exposed electrode, a surface of which is capable of coming into direct contact with the polluted air to be treated, or
   (2) is composed only of said protecting electrode.

10. The apparatus according to claim 5, wherein said low temperature plasma-generating unit contains, in a housing, (a) a solid-cylindrical protecting electrode containing a core electrode and a hollow-cylindrical insulating sheath surrounding a circumference of said core electrode, and (b) a conductive mesh electrode, and the hopcalite catalyst is carried on said conductive mesh electrode while a surface of said catalyst is exposed.

* * * * *